United States Patent [19]

Legorreta

[11] 4,280,623
[45] Jul. 28, 1981

[54] METHOD AND APPARATUS FOR CONTROLLING, ORIENTING AND ANALYZING BIOLOGICAL CELLS IN LIQUID SUSPENSION

[76] Inventor: Gildardo S. Legorreta, 3121 Parana, Providencia, Guadalajara, Jal., Mexico

[21] Appl. No.: 118,340

[22] Filed: Feb. 4, 1980

[51] Int. Cl.³ .......................................... B07C 5/342
[52] U.S. Cl. .................... 209/3.1; 209/44.1; 209/540; 209/932; 209/934; 250/222 PC; 356/72; 235/92 PC; 324/71 CP
[58] Field of Search .................... 209/3, 3.1–3.3, 209/540, 541, 543, 544, 552, 576–579, 588, 606, 906, 932, 934, 127 R, 127 A, 127 C, 44.1; 356/39, 72, 73, 335–343, 440–442, 246; 324/71 CP; 235/92 PC; 250/222 PC, 573, 574, 576

[56] References Cited

U.S. PATENT DOCUMENTS

| | | | |
|---|---|---|---|
| 3,763,428 | 10/1973 | Preist | 250/222 PC |
| 3,770,349 | 11/1973 | Legorreta | 356/73 |
| 3,815,022 | 6/1974 | Golibersuch | 324/71 CP |
| 3,963,606 | 6/1976 | Hogg | 209/3 |
| 4,175,662 | 11/1979 | Zöld | 209/552 |

FOREIGN PATENT DOCUMENTS 1389553 4/1975 United Kingdom .

OTHER PUBLICATIONS

Herzenberg et al., "Fluorescence–Activated Cell Sorting", 3-76, pp. 108–117, Scientific American.

Primary Examiner—Joseph J. Rolla
Attorney, Agent, or Firm—Edwin A. Oser

[57] ABSTRACT

A liquid flow system contains suspended biological cells for the purpose of orienting them, spacing them from each other and analyzing the cells. Many biological cells are not of spherical shape but may be disk-like or rod-like in appearance. The present flow system includes means for orienting the cells with respect to the liquid flow and for either centering them or displacing them into a desired plane within the fluid flow. The cells are electrically charged, suspended in a dielectric fluid and deflected by a suitable electric field. Optionally an image analysis may be performed.

44 Claims, 5 Drawing Figures

METHOD AND APPARATUS FOR CONTROLLING, ORIENTING AND ANALYZING BIOLOGICAL CELLS IN LIQUID SUSPENSION

BACKGROUND OF THE INVENTION

The present invention relates generally to a liquid flow system containing suspended biological cells and particularly to such a system which permits automatic detection of the cells and orientation thereof with respect to the axis of the liquid flow.

Liquid flow systems containing suspended particles such as biological cells are well known in the art at this time. An early flow system of this type is described in one of the Applicants' prior U.S. Pat. No. 3,675,768 and a division thereof U.S. Pat. No. 3,770,349. Since the time of the above referred to United States patents automatic detection of cells for cancer diagnosis and other research programs has become of increasing importance. However, certain problems remain to be solved. Among these problems is the orientation of a cell in the liquid stream when the cell is not spherical.

For the automatic analysis of biological cells suspended in a liquid it is desirable to separate the cells so they flow individually through the liquid. In the past, it has been attempted to disrupt the cytoplasma of the cell to obtain the nucleus of the cell. Blood cells which occur naturally isolated from each other have had the greatest success in liquid flow systems. However, when it is desirable to analyze epithelial cells such as those exfoliated from vaginal epithelia, they must first be processed so as to separate those cells which naturally exfoliate as single or individual cells and to eliminate clumps or clusters. A number of techniques are known for isolating single cells from clumps of cells. These techniques require chemical methods such as treatment with enzymes such as collagenase or hyalorunidase. Also physical methods are known for this purpose such as stirring, irradiating the cells with ultrasound or syringing them. Frequently both physical and chemical methods are required to loosen the cell boundaries.

The preparation of samples for automatic cell analysis may, for example, be described in connection with a collection of cells for cancer detection. Sputum, scrapings from oral mucosa or from the vaginal canal including the cervical opening and the endocervical canal are a complex mixture of epithelial cells which may be rod-shaped, or disk-shaped and may include non-epithelial cells such as spherical leucocytes and disk-like erythrocytes. The size and thickness of the cells depends on the status of the cell differentiation. Most of these cells have a nucleus that contains the most important information with regard of whether the cell is cancerous or not. Also among the cell collections there may be bacterial parasites and mucus. As mentioned before, some cells occur isolated from others while other cells remain attached to each other by their loosened borders; still others occur in clusters which first must be loosened or removed to obtain a suspension of single cells.

Routinely and conventionally the cell samples must be preserved in some manner before the automatic examination can take place. Usually the preservation is accomplished by a fixative chemical such as formaldehyde or ethyl alcohol which coagulates colloids such as proteins. Fixatives and other chemicals change the physical properties of the cell membranes and cause them to be easily permeable by aqueous solutions. Preservation may also be accomplished by other means, for example by refrigeration.

Preservation is required because the samples are taken either at bedside of the patient or in the doctor's office. On the other hand, the cell analysis of all collected samples is usually performed at a different place. Most of the techniques for the isolation of cells are performed on fresh samples before the colloids coagulate. Thus, preferably, the sample preparation is accomplished as close as possible to the time the sample is taken.

For example, most of the uterine or sputum cells to be investigated have the shape of a disk, each cell having a disk-like nucleus. When such cells are attached to a glass surface usually one of the cell's major surfaces sticks to the glass. Because the liquid flow creates hydraulic forces, the cells move parallel to the flow. Hence, for optical image analysis the cell should pass through the focal plane of a microscope. This may or may not be true of cells having a non-spherical shape. If the flow is parallel to the optical axis, the cells are in the focal plane at one instance. However, the nucleus will not present a front image unless the cell has been oriented so that it crosses the focal plane with its major surface parallel to the optical axis. In the prior art this goal has not been attained.

It is accordingly an object of the present invention to prepare biological cells for automatic analysis by separating them from a cell cluster and flattening wrinkled cells.

Another general object of the invention is to control the cells in a liquid flow system by orienting the cells in a desired direction, centering the cells to improve the detection geometry, deflecting selected cells by induction to focus them and spread them in space according to their mass to facilitate sorting of the cells.

SUMMARY OF THE INVENTION

According to the present invention there is provided apparatus or method for orienting biological cells suspended in a dielectric fluid. The fluid is made to flow along a predetermined fluid path.

Furthermore, cells and clumps of cells are charged electrically, that is preferably by an excess of electrons so that they have a negative electrical charge. The charged cells are suspended in a dielectric liquid. The liquid and the suspended cells are forced to move in the direction of gravity, that is downwardly and within an electrostatic field produced by electrically charged plates. Various types of electrostatic fields may be provided in accordance with the present invention. Thus a field may be generated by a ring or two sets of plates which are negatively charged. Alternatively, negatively charged plates may be located on only one side of the cells or else pairs of plates may be used, one being charged negatively and one positively and disposed on opposite sides of the cell's path.

The charged plates act on the electrically charged cells through the dielectric liquid suspending the cells, that is by induction. This makes it possible to center and orient the cells so that all cells of the same shape are moved into the same relative position. Additionally, while moving in the electric field or at the time the cells are electrically charged the clumps of cells which had their boundaries previously loosened will detach from each other so that they become isolated individual cells.

Further, if they have become wrinkled during their previous treatments they are now flattened out.

Thus, it will be seen that the electrostatic treatment of the cells suspended in the liquid is useful for the automatic analysis of cells by many of the apparatus and methods presently available. The problems related to automatic analysis of cells including the problem of orientation of cells have been reviewed in two issues of "The Journal of Histochemistry and Cytochemistry," Volume 24, No. 1, pages 1–414, January 1976, and Volume 25, No. 7, pages 479–952, July 1977.

The novel features that are considered characteristic of this invention are set forth with particularity in the appended claims. The invention itself, however, both as to its organization and method of operation, as well as additional objects and advantages thereof, will best be understood from the following description when read in connection with the accompanying drawing.

DESCRIPTION OF THE PREFERRED EMBODIMENTS

Figure 1A:
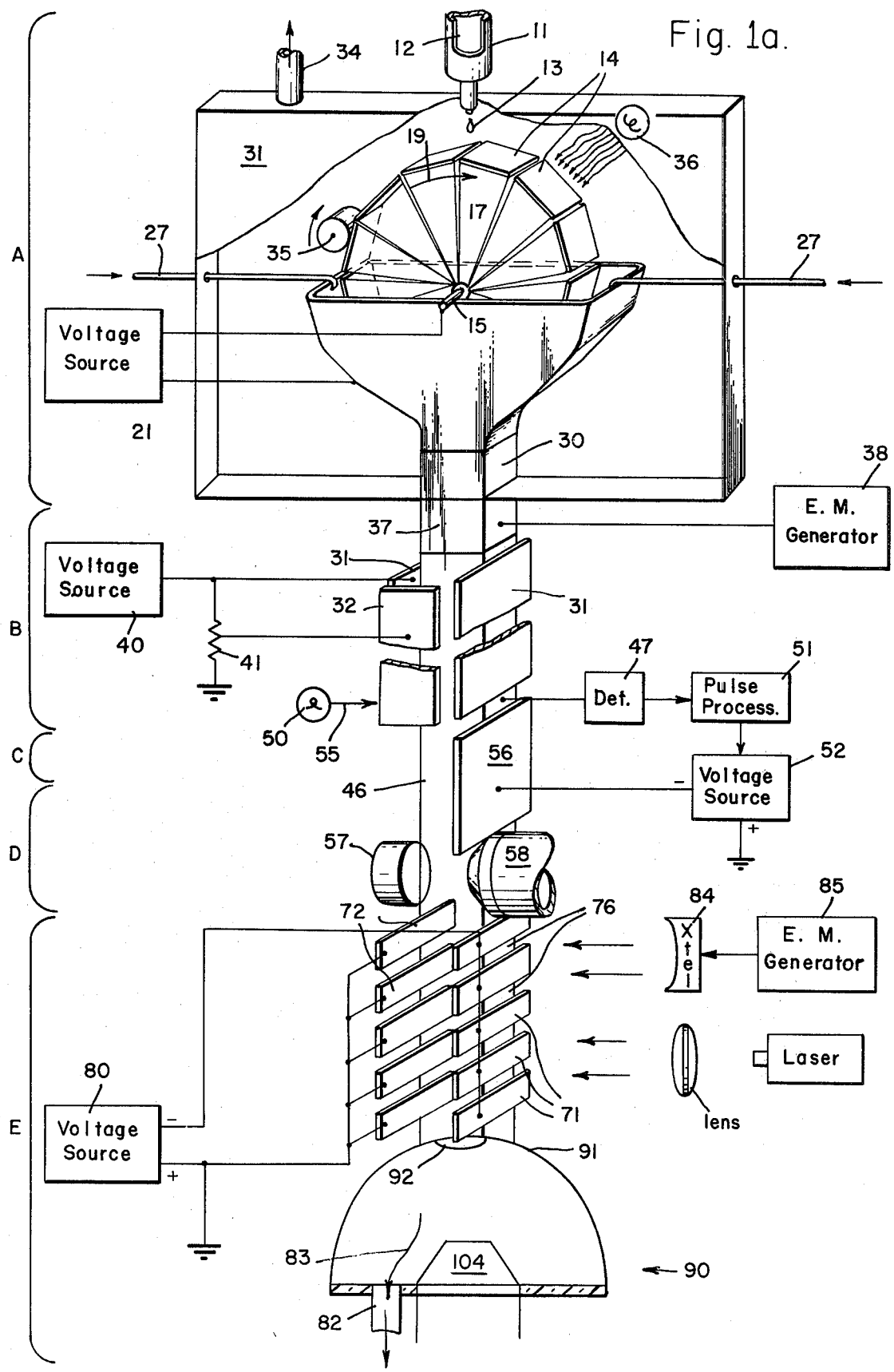
FIG. 1a is a view in perspective of an apparatus in accordance with the present invention, it being understood that some of the portions of the apparatus of FIG. 1 may be omitted for special purposes.

Referring now to the drawings and particularly to FIG. 1, there is illustrated an apparatus embodying the present invention. The apparatus of FIG. 1 is subdivided into sections A, B, C, D and E which may be used separately or some of the sections may simply be omitted. Section A illustrates how the cells originally contained in a concentrated aqueous solution may be charged electrically and preferably negatively, so that each cell has an excess of electrons. Section A also includes a pump for forcing a dielectric liquid in which electrically charged cells are suspended downwardly through a suitable container.

In Section B the suspended cells are subjected to an electric field created by applying a higher voltage to one set of plates than to another set of plates orthogonal thereto. This causes the cells to orient themselves. That is, all cells of the same shape assume the same relative position.

Section C includes a detector which may, for example be an optical detector. The detector will respond to the presence of a cell, its size and structure. Section D includes another electrically charged deflection plate for deflecting the cells into a predetermined plane which is the focal plane of a microscope oriented normal to the direction of flow. The detector of Section C may be coupled to the deflection plate to apply a deflecting voltage upon the presence of a wanted cell which has been selected by the detector.

Finally, Section E includes two sets of plates disposed parallel to each other, one being charged positively and the other negatively. At the same time the cells may be subjected to ultrasonic waves or to electromagnetic waves such as a laser beam. This will now orient the cells so that their large surface is normal to the direction of flow. A microscope is disposed at the end of the flow path for optically analyzing the cells which are directed toward the microscope. The microscope may either work by transillumination or by epiilumination such as disclosed in the Applicant's prior British Pat. No. 1,389,553.

Figure 1B:
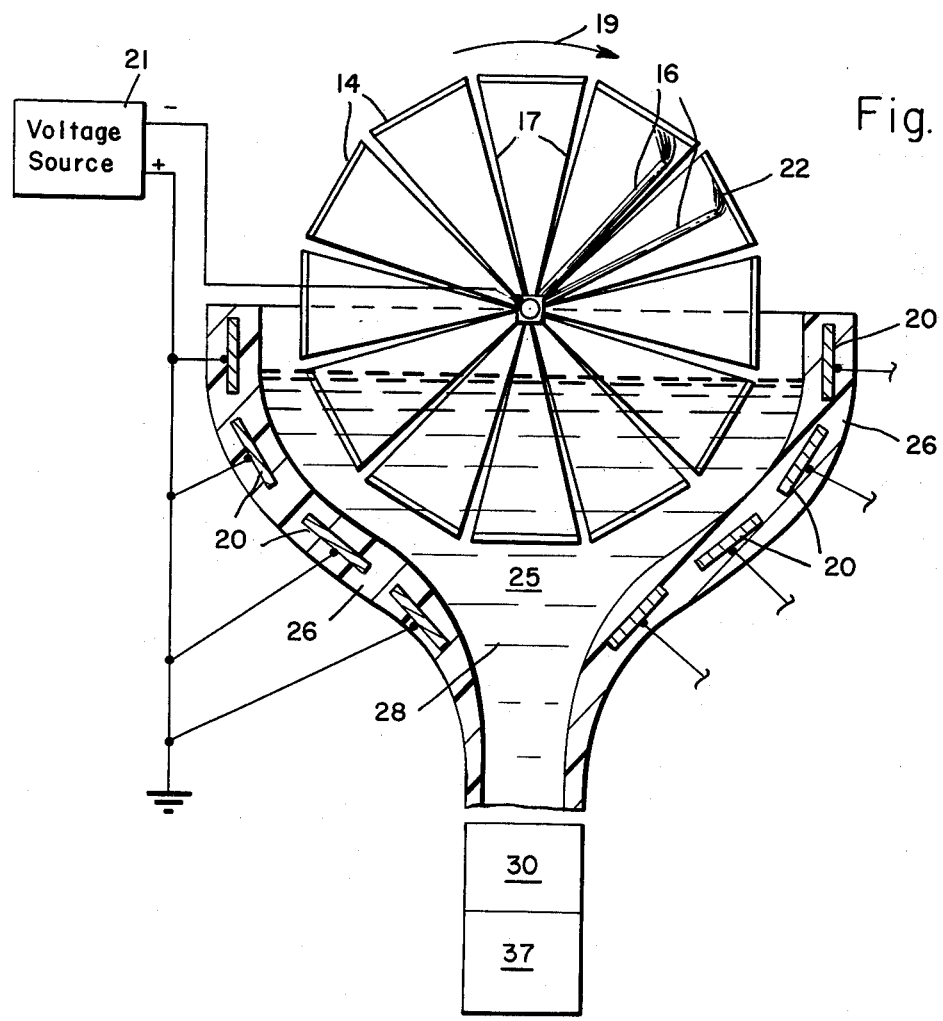
FIG. 1b is an enlarged elevational view of a portion of the apparatus of FIG. 1a used for electrifying the cells.

Referring now in more detail to FIGS. 1a and 1b, and particularly to Section A, it should be noted that this portion of the apparatus preferably is coupled to Section B and may be utilized for the preparation of samples. As indicated before, this should be performed at the time the sample is taken. Hence, this apparatus preferably is disposed close to the place where such samples are taken such as a doctor's office. The samples may initially be treated as outlined hereinabove by chemical or physical means. This will cause the cell boundaries to become loose and to render the cell membranes permeable.

The sample is now contained in a concentrated aqueous solution and may be dispensed from a dispenser 11, such, for example, as a disposable syringe. The dispenser 11 may have a piston 12, the motion of which is controlled in any conventional manner to produce liquid drops such as shown at 13. The sample drops 13 fall on metallic or conductive plates 14 which may, for example, be arranged along a circle. The plates 14 may be insulated from each other in a manner not shown and may be supported by insulating rods 17.

The rods 17 are secured to a central shaft 15 which is rotated in a manner not shown in the direction of arrow 19. Hence, the rotation of the shaft 15 will cause the plates 14 to rotate about a circle. The negative pole of a voltage source 21 is connected to the shaft 15. This will electrically charge stationary conductive bars 16 having brush-like protrusions 22 at their tips so as to impart a negative charge to each plate 14 as it passes one or more of conductive bars 16. Thus, as long as the plates 14 are charged negatively they jointly form a cathode.

Another set of electrodes 20 is disposed opposite the plates 14 in the lower portion of their travel. The electrodes 20 are positively charged by connection to the voltage source 21. The electrode 20 may consist of a single U-shaped piece or of individual plates. If it consists of individual plates, they should be insulated from each other.

The electrodes 14 preferably consist of bare metal so that the cells deposited on the plates or the drops 13 are in direct contact with the metal. On the other hand, the plates 20 should be electrically insulated, for example, by an insulating coating. Hence, the two electrodes 14 and 20 create an electric field like that of a capacitor.

A plurality of conduits 27 are provided for feeding a dielectic liquid 25 from an outside source to the container formed by the electrodes 20 shown separated from each other by an insulating coating (FIG. 1b). The pressure and rate of flow of the liquid 25 will be controlled in some conventional manner. There are lateral walls 26 which may be formed by the insulating coating to hold liquid 25. The entire structure discussed so far is housed in a suitable container or box 31.

The liquid exits through an outlet 28 into a pump 30 which pumps the liquid into the succeeding sections such as Section B. The outlet 28 preferably has a square cross-section as shown. Furthermore, a vacuum may be applied to the container 31 through a conduit 34. A cylinder 35 is provided in contact with the plates 14 as they emerge from their liquid bath. It is rotated in a clockwise direction as shown by the arrow. The cylinder 35 has an absorbent surface so as to clean the plates 14 as they emerge from the liquid 25 and before they are coated again by the drops 13. One or more light sources 36 may be provided for heating the plates 14 either before they are coated by the drops 13 or afterwards or both. The light sources 36 may be infrared lights to provide sufficient heat. Also, the liquid dispensed by the dispenser 11 may be heated.

If the cells are, for example, disk-shaped, one of their main surfaces will adhere to one of the plates 14. The suspending liquid will rapidly evaporate due to the elevated temperature of the suspending liquid, the hot temperature of the plates and the low pressure created by the vacuum line 34. When each plate reaches the brushes 22 which, of course, are stationary, it is electrified and the attached cells are provided with an electric charge.

Since the cells now have the same electric charge they repel each other. This causes the cells, the boundaries of which have previously been loosened, to separate from each other. At the same time, those cells which may have become wrinkled become flat. Those cells which have previously been prepared to disrupt their cytoplasma and free their nuclei do so by the effect of the electric charge. The evaporation continues until the cell is attached to the plate by a small amount of liquid which finally also evaporates. Thus the cathode 14 consisting of the plates, together with the anode consisting of the plates 20 of opposite polarity furnishes the electric charge of the cells.

Since the cells have the same electric charge they repel each other. At the same time the oppositely charged electrode 20 attracts the cells. Hence, when the adhesion forces that attach the cells to the plates 14 is diminished by evaporation, the cell is ejected and attracted by the plates 20 and is washed off by the liquid 25 which issues from the pipes 27.

Reference is now made to Section B of FIG. 1. This is designed to produce a multiple electrostatic field which tends to repel the cells by induction on the negative charged cells. The liquid is forced by the pump 30 downwardly. An electromagnetic generator 38 is provided which is coupled to a plurality of ultrasonic devices 37 such as quartz crystals which are oriented and shaped to produce parallel waves coaxial with the cell path. The ultrasonic device 37 has a suitable central orifice to permit the suspending liquid to pass. Instead of utilizing ultrasound it is also feasible to provide a parallel coaxial beam of laser rays.

Downstream of the ultrasonic device 37, two parallel conductive plates 31 are disposed which are charged negatively by a voltage source 40. Another set of plates 32 is provided parallel to each other and at right angles to the plates 31. The plates 32 are charged negatively but at a lower voltage as indicated by the voltage divider 41. The positive terminal of the voltage source 40 is grounded as shown. It will be understood that the plates do not have to be arranged in a square or rectangular formation, but they may have a circular or oval outline formed by four or more plates. The length of the plates depends on the particular function of the apparatus. It should be much larger than shown at FIG. 1a as indicated by the fact that the plates are shown separated from each other by broken lines.

Figure 2:
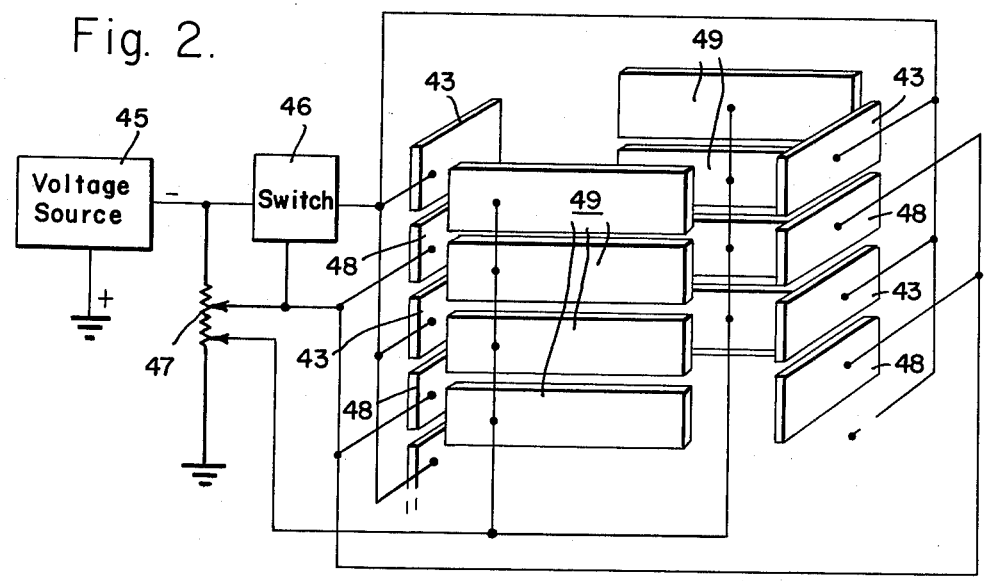
FIG. 2 is a plan view of an alternative spaced set of plates for applying an electrostatic field.

Instead of using the solid set of plates 31, 32 it is preferred to use the space bars illustrated at FIG. 2. As shown there, each plates 31 or 32 is replaced by two sets of bars 43 and 48. Each set of bars 48 are provided with a relatively low negative voltage obtained from voltage source 45 and voltage divider 47. The positive terminal of the positive source 45 is grounded as shown.

The bars 43 are provided normally with a higher negative voltage from the voltage source 45. However, by means of switch 46 the high negative voltage is periodically turned off and replaced by a low negative voltage which is the same as that applied to bars 48.

Thus, the two sets of bars 43 and 48 are both at one time charged with a relatively low negative voltage. Periodically, however, the bars 43 are provided with a high negative voltage. There are a pair of sets of bars 49 orthogonal to sets 43, 48 to make a rectangular array. All bars 49 are supplied with the same voltage that is lower than the voltage of bars 48 as indicated by the lower tap on voltage divider 47.

The thus generated electrostatic field has two functions. In the first place it will help to space the cells from each other by a predetermined space or predetermined time period. In the second place, because there is always a relatively low negative voltage, the cells do not have an opportunity to become disoriented, that is they will not deviate from the desired orientation, nor move out of the center.

It will be understood that all the plates 31 and 32 shown in FIG. 1 will be identical with the set of bars 43, 48 and 49 of FIG. 2. This arrangement is a preferred arrangement.

It will, of course, be understood that the switch 46 is operated at suitable time intervals to obtain the desired spacing between cells. Also, the sets of plates such as 31 and 32 of FIG. 1 need not necessarily be square, but could be circular or oval.

Both sets of plates 31 and 32 or 43, 48 and 49 are coated with insulating material and properly connected to the voltage source 40 or 45. The thus created electrostatic field repels the negatively charged cells by induction. Since there are two sets of plates 31 and 32 it may be called a multiple repelling field. Since one pair of plates 31 (or 43, 48) has a higher negative charge than the other set of plates 32 (or 49), the electrostatic repulsion between the plates 31 (or 43, 48) is stronger than that between the plates 32 (or 49). As a result, the negatively charged cells are oriented, that is, all cells of the same shape are in the same relative position.

Additional inlets may be provided to fill the space between the plates 31 and 32 entirely with a dielectric liquid. This may be the same liquid as the liquid 25. Conventional bubble traps may be provided to extract air. The entire structure of Sections B-E may be enclosed in a suitable container 46. The ultrasound device 37 is in contact with the dielectric liquid and hence transmits the sound waves.

It should be noted that the physical size of the container 46 and of the plates 31 and 32 is not shown to scale. By way of example, the container 46 may have an overall length of 50 centimeters and may have a cross-section of 1 centimeter squared. This is particularly true of the plates 31 and 32 which have been shown broken off to indicate that they are much longer than shown.

It will be apparent that the container 46 must be transparent to the electrostatic field, that is it should consist of an insulating material. The purpose of this wall 46 is to maintain the fluid containing the suspended cells apart and within the plates for generating an electric field.

The electrostatic repelling field which is traversed by the dielectric liquid flowing downwards is stronger between the plates 31 (or sets 43 and 48) than between the plates 32 (or set 49). As soon as the cells are charged with electricity of the same polarity of that of the field they are repulsed by the field and eventually the cells are centered along the axis where the electrical forces of the field are in equilibrium. The equilibrium may exist in the geometrical center of the two sets of plates. This centering which is due to induction is applied to all types of electrified cells regardless of their shape, that is whether they are spherical or non-spherical. It will be understood that it is a very useful result that the cells are centered within a fixed linear path. This is highly useful for the further automatic orientation and segregation of the cells. In addition, the inductive action of this repulsive field produces an orientation of the cells.

This orientation causes all cells which have a non-spherical shape to assume the same relative position within the path of the cells.

A number of forces act on the orientation of the cells. In the first place, the hydraulic forces due to the downwardly flowing liquid causes suspended cells to rotate so that they present the least resistance due to hydraulic forces. This orientation force has been frequently used in the past for causing cells to cross the focal plane of an optical detector. However, orientation due to the hydraulic forces is insufficient because a non-spherical cell, say a disk-shaped cell may rotate through 360° similar to a coin being rotated on a table; is is supported at its side and still rotates within a sphere due to its rotation. This change in position of a disk-shaped cell produces an error in the optical detector which is greater than the difference between normal and abnormal cells to be detected.

To the action of the hydraulic forces there is added the action of the repulsive electrostatic field. As explained before, this is greater in one direction. It acts differently on spherical cells where the excess of electrons is evenly distributed than on cells of non-spherical shape where the electrons are distributed unevenly but with the same distribution for cells having the same shape. Therefore, all cells of the same shape are oriented or moved into the same relative position.

A parallel ultrasound beam aids in the orientation. In the first place, the vibrating effect due to the sound waves overcomes the initial inertia of a cell. Since the waves are parallel to each other and coaxial with the cell path, this results in the tendency to place the cells in the same relative position. Due to the fact that laser rays have a much shorter wavelength, they have a smaller vibratory capacity. Nevertheless, they have the same orientation effect even though smaller. The same is true of other types of high frequency electromagnetic waves such as microwaves.

From the above, it will be apparent that the multiple repulsive electrostatic field has both a centering and an orienting effect. Other effects which may be useful for the automatic analysis of particles such as cells will now be discussed.

It is possible to isolate individual cells so that they are separated from each other in the liquid suspension by an equal length, that is by an equal time when they reach the detector. To this end preferably the grill plates 43 of FIG. 2 are used. This will result in an electric field which might be called to have a grill pattern. In order to isolate the cells as they pass in the suspending liquid the bars 43 must be alternately and successively turned from the lower to the higher voltage. This, of course, will similarly turn the electrostatic field alternately low and high which produces a separation of the cells along their flow path.

If the concentration of the cells is sufficiently low the cells are separated from each other by equal lengths corresponding to equal lengths of time or multiples of such times. For this reason the cells are single rather than two or three occurring simultaneously. This action might be called the isolation of the cells or their individual spacing resulting in a desired timing of the cells. Under the action of the electrostatic plates 31, 32 the cells unwrinkle and become flat or ironed provided they have not previously been hardened by fixatives. At the same time if some of the cells remain still attached to each other by their loosened boundaries, they repel each other so that they become detached. Accordingly, it will be seen that Sections A and B have at least in part the same functions; namely, the flattening of individual cells and detaching of cells which were originally in a clump or cluster. At this point the procedure may be stopped.

It should be noted that after the cells have been prepared in a doctor's office apparatus consisting of Sections A and B may be used with a bottom portion suitable to let suspended liquid out in drops; they may be poured drop by drop into a liquid fixative. Thereafter, they may be sent to a laboratory for further processing. Alternatively, drops containing single flattened cells may be deposited on quartz or glass slides or on a transparent tape for solid substrate automatic analysis. Thus it will be realized that the difference with a cell suspension that has not been treated in Sections A and B is, the greater yield of single flat cells, better suited for automatic analysis.

The preparatory apparatus of Sections A and B is necessary because both enzymatic, electrostatic separation of cells, as well as flattening of cells, is better accomplished in fresh unhardened cells.

Sections A and B will usually be used together either alone or with other sections such as the subsequent Sections C, D and E.

Whenever a sample is to be analyzed after fixation and storage it has to be further processed whereby the cells may have to electrically charged again. This may be accomplished either with the apparatus of FIGS. 1a, 1b, Section A or apparatus of FIG. 3, Section F.

Figures 3, 3A:
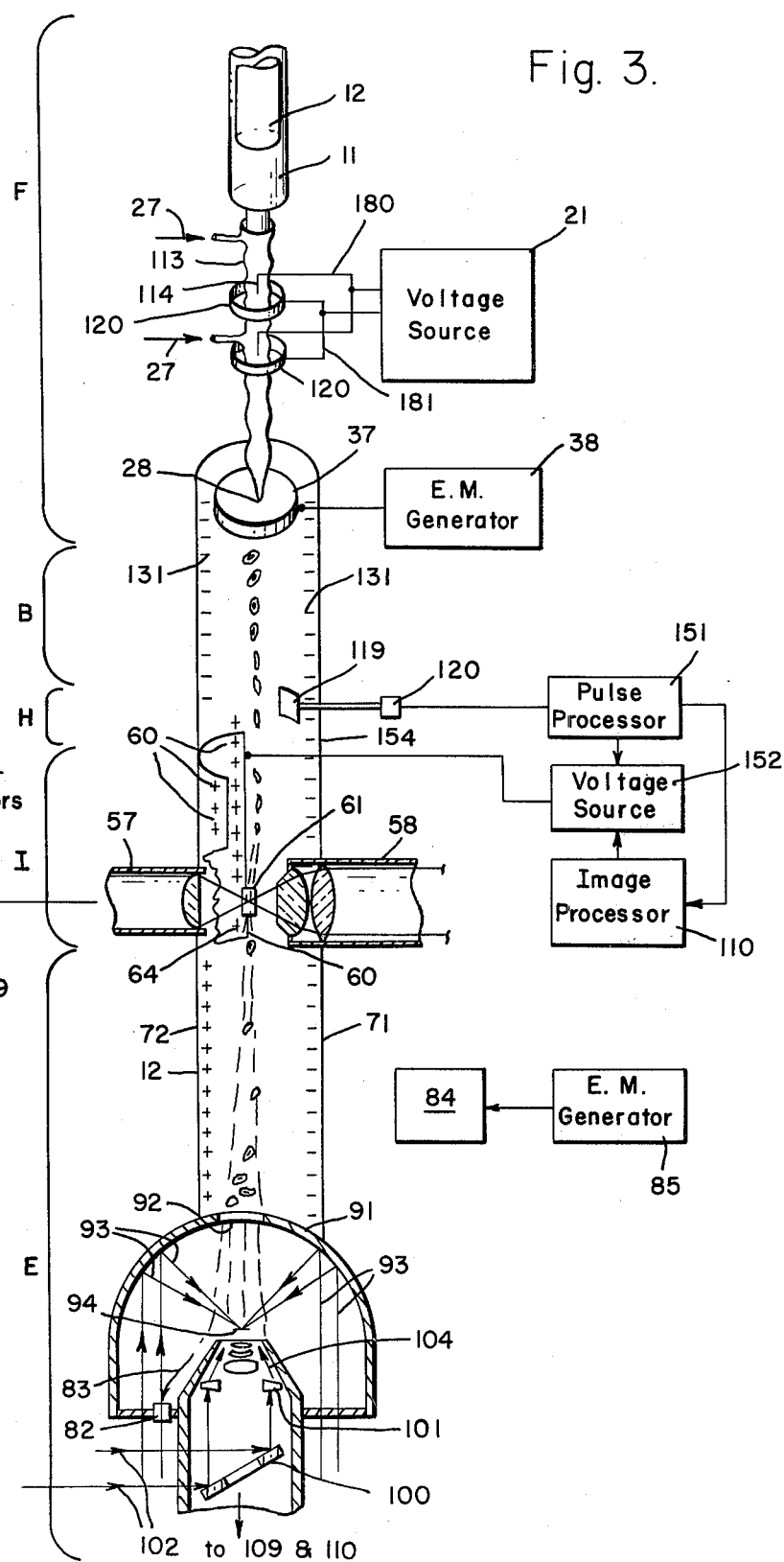
FIG. 3 is a schematic elevational view somewhat similar to the apparatus of FIG. 1 but illustrating various alternatives thereto.
FIG. 3a is a top plan view of a portion of the apparatus of FIG. 3.

Referring now to FIG. 3, and before describing the further Sections C, D and E of FIG. 1, an alternative way of electrically charging the cells wil now be explained. The apparatus of FIG. 3 corresponds in part to that of FIG. 1. Thus the apparatus has a Section F, a Section B corresponding to Section B of FIG. 1, a Section H, a Section I and Section E corresponding to that of FIG. 1.

The cells are again suspended in an ordinary liquid and are injected as before through inlet 11 which may be a disposable syringe having a plunger 12. At the same time a dielectric liquid is injected as before through inlets 27. The mixing of the two liquids is promoted by the irregular shape of tube walls 113 which have convex and concave portions to provide restrictions and dilations of the liquid. This is equivalent to the syringing of the suspension. However, it will be understood that any number of known means may bbe used for this purpose such as ultrasound waves.

The thus mixed liquid flow past a central needle-shaped electrode 114 which is connected by leads 180 to the negative pole of voltage source 21. A ring-shaped outer electrode 120 is connected by leads 181 to the positive pole of the source 21 and is disposed about the insulated walls of tube 113. As shown in FIG. 3, there may be two or more spaced pairs of these electrodes 114, 120 to provide electrical fields.

Disposed below the two pairs of electrodes 114, 120 there is an ultrasound source 37 which is fed by an energizing electromagnetic generator 38. The ultrasound source 37 is arranged to provide parallel waves which are coaxial with the cell path. In other words, the generator should have a concave mirror geometry.

The sample may be analyzed in Section B which is identical to that of FIG. 1. Instead of illustrating the plates which generate electric fields, the field has been represented by a plurality of negative signs (−) 131. A set of cells is also shown schematically and not to scale to illustrate how the cells become oriented by this field. It also illustrates that the cells have been subjected to electrostatic fields which are alternately turned high aand low so as to provide an equal distance between cells or an equal time interval.

By way of example, Section C may be an optical sensing station as illustrated in FIG. 1a and which will be described subsequently or a electromagnetic sensing station H such as shown in FIG. 3.

The optical sensing Station C of FIG. 1a includes a suitable light source 50 generating a light beam which passes through the container 46. The light beam 55 impinges on the passing cells and on the optical detector 47 that produces electric pulses. The detector 47 is connected to a pulse processor 51 capable of turning the voltage source 52 off and on. This in turn charge a deflection plate 56 with a negative charge in response to the cell detected by the detector 47 and the output of pulse processor 51.

The detector 47 may detect, for example, light scattering, light absorption by unstained or stained cells luminescence or fluorescence of cells which have previously been stained by a fluorescent dyestuff. It will also be understood that one or more detectors 47 may be provided. Depending on the signals obtained from detector 47 which depend on the optical properties of cells and amplified and processed by signal or pulse processor 51, they may be displayed as a histogram which may be compared to normal population histograms. Generally, the cells are stained with a fluorescent dyestuff which operates on the nucleus.

It will be readily appreciated that the efficiency of most optical detectors will be increased by the orientation of the cells because incident light impinges on all cells having the same relative position. The efficiency is further increased by confining the cells to a narrow linear path so that all cells are subjected to a light probe in the same geometry. Hence the efficiency of the sensing station is increased by the isolation and timing of the cells because the possibility of duplets, triplets or more cells occurring close together is reduced; the cells reach a sensing zone with equal time intervals. This time interval may be controlled to match the process time of a pulse processor or analyzer. A good review of available detectors may be found in the above-cited issues of Journal of Histochemistry and Cytochemistry. it is obvious that electrostatic fields described here can be used with most of the flow systems with minor changes.

Instead of utilizing an optical detector an electromagnetic detector such as shown in Section H of FIG. 3 may be used. The electromagnetic detector is responsive to the electrons which are distributed over the cell surface depending on the cell shape. Thus spherical leucocytes have electrons which are evenly distributed over the surface. The electrons of diskshaped epithelial cells have the electrons concentrated on their rim while electrons of rod-shaped cells are primarily distributed at opposite edges.

Thus a conventional electromagnetic sensor 119 may be located at the same place as the optical sensor 47 of FIG. 1. It provides electrical signals at the device 120 which may be processed the same way the signals from detector 47 are processed. It will be understood that the resolution of electromagnetic sensors depends on their number and distribution. If it is only a single sensor a simple parameter such as cell size may be measured. If there is a multiplicity of sensors, cell shapes may be detected. In this case, the plates 31, 32 of FIG. 1 are alternately turned on and off and the detector senses during the off periods. The ultrasound may operate continuously or only during the off periods. The sensors of electric charge of the cells produce a signal that may be fed back to an optical sensor in order to select, for example by size, a cell to be optically analyzed and cells or debris which should be ignored. Such a program depends on the particular purpose of the apparatus based upon the principles of the present invention.

Section D of FIG. 1a will now be explained. This section illustrates a particular manner of producing electrostatic deflection of cells that have been centered and oriented by Section B. To this end there is provided a metallic or conductive plate 56 which is disposed along the plane of one of the plates 31, that is one of the plates having a higher voltage applied thereto. Metallic plate 56 is electrically insulated from the liquid by an insulating coating and is connected to the negative pole of voltage source 52, the positive pole being grounded. It will be understood that there is only a single plate 56.

It will be understood that when the plate 56 is properly energized it will repel cells of equal negative charge to cause the cells to deflect.

FIGS. 3 and 3a show an alternate way of producing a deflection of a negative cell by pulling it by a positive plate or plates 60. To this end there are two sets of positive charged plates 60. Each set is disposed above and below the optical axis and along the cell path. The two positive forces pull the negative cell and produce a resultant movement between the forces that carry the cell through the optical plane. However, the last in the row of positive plates 64 may be activated independently from the other Plate 64 in the opposite row of plates 60 pulling to one or the other side for sorting purposes according to the result of a particular cell analysis thus sorting a wanted cell into a receptacle, not shown, for further examination. It is obvious that negative push and positive pull may be used together as shown in Section I.

The electrostatic deflection of cells suspended in the liquid is rather sluggish and is useful only for creating small displacements. For example, as shown in FIGS. 1a and 3, it is used for focusing a cell within the focal plane of a complex optical system such as a microscope. The microscope has an objective 57 with a front lens and an illuminator such as a light condenser 58. It will be understood that the lens of the condenser 57 should be as closely as possible to the wall 46 which, of course, must be transparent to light. Similarly, the front lens of the objective 57 of the condenser 58 should be as close as possible to the wall 46 which, of course, must be transparent to light. The focus of the microscope objective may be defined as a zone in which an object produces a bright, sharp image through the microscope lens. The focal plane has a depth 61 not represented to scale. Hence, the inductive action of plate 56 (or plates 60) may be used to cause a cell to cross the focal depth from one side to the other of the focal plane, thereby producing for an instant a sharp image through the microscope. It will be realized that for image analysis a sharp image is necessary.

Preferably, the microscope 57, 58 is used in combination with the detecting station C or H of FIGS. 1a and 3. Optical detectors of Section C are preferably of the so called "zero resolution" type. To this end the analysis obtained from the pulse processor 151 is fed back to the voltage source 152 to turn it on and to produce a deflection only of an interesting cell. At the same time the photodetectors 109 in the image plane of the microscope are actuated. For example, cells passing the first detection station of Sections C or H are selected say, according to their size and deflected through the microscope focus for a more time consuming process, for example, for image analysis. In other words, the first detection station actuates a shutter of the image analysis device 110.

So far, the description has dealt with the manipulation or control of electrified cells by means of a double repellant field in Section B and by means of a single repellant field in Section B and a single pulling field of FIG. 3a. The operation of a positive-negative electrostatic field as shown in Section E will now be described.

To this end there are provided two sets of parallel, spaced plates 71 and 72. Plates 71 are charged negatively by the voltage source 80 while plates 72 are charged positively by the same voltage source. Again, the plates are coated with an electrically insulating material to prevent the passage of current therebetween. It is preferable to have plates 71 and 72 divergent. The plates surround the container 46 which is provided with an outlet 82 at the bottom. This will permit the cell suspending liquid to exit from the apparatus.

The plates 71 and 72 which are respectively charged negatively and positively are preferably separated by a plurality of gaps 76 to provide a grid-like construction of the type shown in FIG. 2. These windows 76 serve the purpose to permit ultrasound to pass therebetween which may be generated by a crystal 84 connected to an electromagnetic generator 85. Alternatively, a parallel laser beam may be generated by a laser 86. Preferably, the beams may be turned on and off at will.

Preferably, if Section E is connected to Section B the ultrasonic beams produced by crystal 37 and generator 38 are inoperative. The ultrasound or laser beams of Section E have an axis normal to the cell path. Hence, the source of vibrating energy has an axis orthogonal to the axis of the cell path. As clearly shown in FIG. 3, the cells spread under the influence of the negative-positive electrostatic field. It should be noted that plates 71 and 72 are not shown to scale. Their length may be increased according to the amount of spread and the desired separation. For wide spread the plates 71 and 72 must have a slight divergence. The deflection of the cells may take several milliseconds to produce a large spread. However, since there are a large number of cells being deflected simultaneously the total number of cells being processed does not depend on the deflection speed.

The cells which have been spread may be collected or sorted by different spaced outlets, not illustrated, for further study.

Alternatively, an inverted microscope 90 may be disposed at the bottom of the apparatus for optical analysis. The microscope 90 has an optical axis substantially coinciding with the cell path. The use of microscope 90 excludes the provision of the microscope of Section D.

It should be noted that it is possible to use cells having a naturally occurring electrical charge. In this case, the cells need not be especially charged as described in Sections A and F.

It should be noted that the cells are deflected by the apparatus of Section D after being electrified in Section A or Section F. On the other hand, in Section E there is both a cell deflection and an orientation of the cells. At the bottom of Section E the cells are oriented so that they are head on with respect to the microscope 90 so that disk-like cells, for example, have one of their main surfaces disposed perpendicular to the cell path.

Preferably, the microscope 90 is of the epiillumination type as described in the Applicant's prior Birtish patent above referred to. Accordingly, the illuminated light originates from the objective and impinges on the front of an object in the focal plane. This is the normal manner of observing opaque bodies such as metals. In other words, this is the opposite of the conventional transillumination of the medical microscope. As shown in FIG. 3, the microscope includes a 45° mirror 100 and prisms 101 to direct the light from an outside light source shown by the lines 102 to an object crossing the focal plane of the objective 104. It will be understood that the epiillumination may be used by itself or in combination with the transiillumination type microscope.

When the epiillumination is used alone, it is useful for cells dyed with a fluorescent dyestuff.

For light absorption and image analysis techniques transillumination is preferably used. For this purpose there may be provided a concave mirror 91 which reflects incident rays of a light source shown by the light rays 93 on the focal plane 94 of the objective 104. The concave mirror 91 has a central opening 92 in the path of the cells. Therefore, microscope and cell path are coaxial. The epiillumination may be used as a shutter of the transillumination analysis system. For example, in an epiillumination system arranged to detect cells on the edge or entering the focal plane, a light scattering arrangement of the known type may be used to select cells for image analysis on the basis of their size.

Thus, negatively charged cells flowing downwardly from Section B may be connected directly with Section E whereby Section D may be omitted. The plates 71, 72 attract and repulse respectively the cells. Accordingly, the cells spread depends, among other factors, on the mass and the amount of charge of each cell. The negative-positive electrostatic field in combination with the ultrasound or laser parallel beam, produces an orientation of the nonspherical cells. All cells with the same distribution of electrons assume the same relative position.

Oriented and spread cells cross the central hole 92 of mirror 91 and eventually the focal plane 94 of the objectivve 104 of the microscope 90. Suspended cells are discharged through suitable outlets 82 represented by arrow 83 or are sorted selectively by means of known methods in accordance with the result of cell analysis. Thus, cells spread according to their mass and the characteristics of electric charge cross the focal plane of the microscope producing for an instant a sharp image.

Spreading of the cells causes the cell image to be formed in different regions of the focal plane. In different samples cells are of different importance. For example, in heterogenous cell populations like sputum or vaginal samples for cancer detection, the spread of the cells causes leucocytes and debris to cross the focal plane in a different area than the heavier epithelial cells. This makes it possible to ignore unwanted cells and to analyze only the image of the interesting cells. Furthermore, the wanted cells are restricted to smaller, cleaner areas. It will be understood that it is possible to apply particular logic or strategy image analysis to different areas. For example, the area of striped nuclei may be analyzed by a different strategy than the parabasal cell zones. For image analysis techniques, refer to the cited Journal of Cytochemistry and Histochemistry.

What is claimed is:

1. Apparatus for orienting, spacing and analyzing cells including:
   (a) means for electrically charging cells to a predetermined polarity;
   (b) means for separating cells from a cluster of cells, and for flattening the separated cells;
   (c) means for suspending the separated and charged cells in a first dielectric liquid;
   (d) means for forcing the liquid downwardly; and
   (e) means for establishing an electric field to repel the charged cells.

2. Apparatus as defined in claim 1, wherein said means for separating the cells includes a series of conductive plates, means for moving said plates through a predetermined path, means for applying cells to be separated in a second suspending liquid upon said plates at a predetermined place, and means for electrically charging the plates to a predetermined polarity to charge the cells.

3. Apparatus as defined in claim 2, wherein means are provided for heating said plates to evaporate rapidly the second suspending liquid of the cells.

4. Apparatus as defined in claim 2, wherein means is provided for cleaning the plates before they reach the point where the suspended cells are applied.

5. Apparatus as defined in claim 2, wherein a second set of plates is provided opposite a portion of the path of said first plates and means for charging said second set of plates to the opposite polarity of that of said first set of plates.

6. Apparatus as defined in claim 2, wherein separated and flattened cells are treated with a fixing substance.

7. Apparatus as defined in claim 1, wherein said means for separating cells includes an ultrasound source.

8. Apparatus as defined in claim 7, wherein said ultrasound is substantially concentric to the flow path of said cells.

9. Apparatus as defined in claim 1, wherein said means for electrically charging cells includes a point-like electrode extending into the first dielectric liquid and a counter electrode surrounding the liquid, and means for creating an electric potential between said electrodes.

10. Apparatus as defined in claim 9, wherein a tubular conduit is provided upstream of said means for forcing and having successive restricted and expanded portions for guiding the first dielectric liquid and the cells suspended therein.

11. Apparatus as defined in claim 1, wherein said means for forcing said liquid includes a pump.

12. Apparatus as defined in claim 11, wherein downstream of said pump there are provided two sets of plates, each set being disposed substantially parallel to each other and the two sets substantially normal to each other, said sets of plates being electrically charged to the same polarity thereby to orient the cells substantially parallel to the direction of the flow path.

13. Apparatus as defined in claim 12, wherein one set of plates is supplied with a higher voltage than the other.

14. Apparatus as defined in claim 13, wherein each of said sets of plates consists of substantially parallel bars substantially equally spaced from each other and forming substantially equal gaps therebetween.

15. Apparatus as defined in claim 14, wherein means are provided for supplying alternate bars of a first set of plates respectively with a higher and a first lower voltage, means for reducing the higher voltage periodically to said first lower voltage, and means for supplying the bars of the second set of plates with a second voltage lower than said first lower voltage.

16. Apparatus as defined in claim 13, wherein the voltage applied to said plates is periodically turned on and off.

17. Apparatus as defined in claim 16, wherein a single deflector plate is disposed downstream of said pair of plates.

18. Apparatus as defined in claim 17, wherein a control voltage is applied to said deflection plates in response to a signal obtained from said detector.

19. Apparatus as defined in claim 12, wherein a detector for the cells is disposed downstream of said plates.

20. Apparatus as defined in claim 19, wherein said detector is an optical detector including a light beam.

21. Apparatus as defined in claim 19, wherein said detector includes an electromagnetic sensor.

22. Apparatus as defined in claim 19, wherein the electric charge of said plates is periodically turned off when said detector is energized.

23. Apparatus as defined in claim 19, wherein a microscope is provided having an optical axis normal to the flow path of the cells for analyzing characteristics of the cells.

24. Apparatus as defined in claim 12, wherein two additional sets of plates are provided downstream of said first set of plates, each set of said additional plates being charged with a polarity opposite that of the other set of plates, thereby to orient the cells substantially normal to the direction of the flow path.

25. Apparatus as defined in claim 24, wherein means is provided for generating ultrasound substantially normal to the direction of flow of the cells, said ultrasound means being disposed adjacent said additional set of plates.

26. Apparatus as defined in claim 24, wherein means is provided by generating a laser beam substantially normal to the direction of flow of the cells and adjacent said additional sets of plates.

27. Apparatus as defined in claim 24, wherein barrier means is provided in the liquid and downstream of said additional sets of plates, and means for activating each additional set of plates independently of the other, thereby to selectively deflect cells for sorting them across one side or the other of said barrier means.

28. Apparatus as defined in claim 24, wherein a microscope is provided having an optical axis substantially parallel to that of the flow path.

29. Apparatus as defined in claim 28, wherein said microscope is of the epiillumination type.

30. Apparatus as defined in claim 28, wherein said microscope is of the transillumination type.

31. Apparatus for orienting and spacing cells including:
   (a) means for electrically charging the cells;
   (b) means for suspending the charged cells in a dielectric liquid;
   (c) means for causing the liquid with the suspended cells to move along a predetermined flow path; and
   (d) means for orienting the cells suspended in the liquid in a predetermined direction with respect to the direction of the flow path.

32. Apparatus as defined in claim 31, wherein said means for orienting includes two sets of plates, each set being disposed substantially parallel to each other and the two sets substantially normal to each other and means for charging the sets of plates electrically to the same potential, thereby to orient the cells substantially parallel to the direction of the flow path.

33. Apparatus as defined in claim 31, wherein said means for orienting includes two sets of plates, means for electrically charging each set of said plates with a polarity opposite to that of the other set of plates, thereby to orient the cells substantially normal to the direction of the flow path.

34. Apparatus as defined in claim 31, wherein a microscope is provided having an optical axis substantially normal to the flow path and disposed downstream of said set of plates to provide an optical analysis of the cells.

35. Apparatus as defined in claim 34, wherein a microscope is provided downstream of said set of plates having an optical axis substantially parallel to the flow path for optically analyzing the cells.

36. The method of orienting, spacing and analyzing cells comprising the steps of:
   (a) separating a clump of cells to provide individual cells;
   (b) applying an electric charge to the individual cells;
   (c) suspending the separated and charged cells in a dielectric liquid;
   (d) moving the cells and the dielectric liquid downwardly; and
   (e) applying a unipolar electric field normal to the direction of flow of the cells.

37. The method defined in claim 36, wherein the clump of cells is separated by electrically charging the cells to the same polarity.

38. The method defined in claim 36, wherein the separated cells are detected and the detected cells are deflected into a predetermined plane.

39. The method defined in claim 36, wherein the cells are additionally oriented by the application of ultrasound thereto.

40. The method defined in claim 36, wherein the cells are additionally oriented by the application of a laser beam thereto.

41. The method defined in claim 36, wherein the cells are oriented substantially normal to the direction of flow by the provision of an electric field.

42. The method defined in claim 41, wherein the oriented cells are optically analyzed parallel to the direction of flow.

43. The method defined in claim 36, wherein the cells are oriented substantially parallel to the direction of flow.

44. The method defined in claim 43, wherein the oriented cells are optically analyzed in a direction substantially normal to the direction of flow.

* * * * *